(12) United States Patent
Jorritsma

(10) Patent No.: US 8,085,395 B2
(45) Date of Patent: Dec. 27, 2011

(54) INSPECTION DEVICE

(75) Inventor: Minne Jorritsma, Nigtevecht (NL)

(73) Assignee: HD Medi B.V., NJ Lelystad (NL)

( * ) Notice: Subject to any disclaimer, the term of this patent is extended or adjusted under 35 U.S.C. 154(b) by 304 days.

(21) Appl. No.: 12/441,437

(22) PCT Filed: Sep. 7, 2007

(86) PCT No.: PCT/NL2007/050438
§ 371 (c)(1),
(2), (4) Date: Mar. 16, 2009

(87) PCT Pub. No.: WO2008/033019
PCT Pub. Date: Mar. 20, 2008

(65) Prior Publication Data
US 2010/0045976 A1 Feb. 25, 2010

(30) Foreign Application Priority Data
Sep. 14, 2006 (NL) ...................................... 1032492

(51) Int. Cl.
*G01N 21/00* (2006.01)
(52) U.S. Cl. .................................................... 356/240.1

(58) Field of Classification Search ....................... None
See application file for complete search history.

(56) References Cited

U.S. PATENT DOCUMENTS

| 6,505,461 | B1 | 1/2003 | Yasunaga |
| 2006/0213816 | A1 | 9/2006 | Jorritsma |

FOREIGN PATENT DOCUMENTS

| JP | 2004 269008 | 9/2004 |
| WO | 2004 072626 | 8/2004 |
| WO | 2005 017814 | 2/2005 |

*Primary Examiner* — Gregory J Toatley
*Assistant Examiner* — Amanda Merlino
(74) *Attorney, Agent, or Firm* — Oblon, Spivak, McClelland, Maier & Neustadt, L.L.P.

(57) ABSTRACT

What is disclosed is an inspection device and a method wherein interconnected, substantially flat bags are provided, in which bags objects are present which are set vibrating, after which one or more images of the objects in the bag are recorded. The vibration is exerted on the objects in the plane of the interconnected bags, whilst a squeezing force effected by means of a pulling force on the bags is exerted on the vibrating objects. The combination of said vibration and said squeezing force on the objects, such as tablets, leads to a quiet and reliable inspection device.

20 Claims, 1 Drawing Sheet

INSPECTION DEVICE

Figure 1:
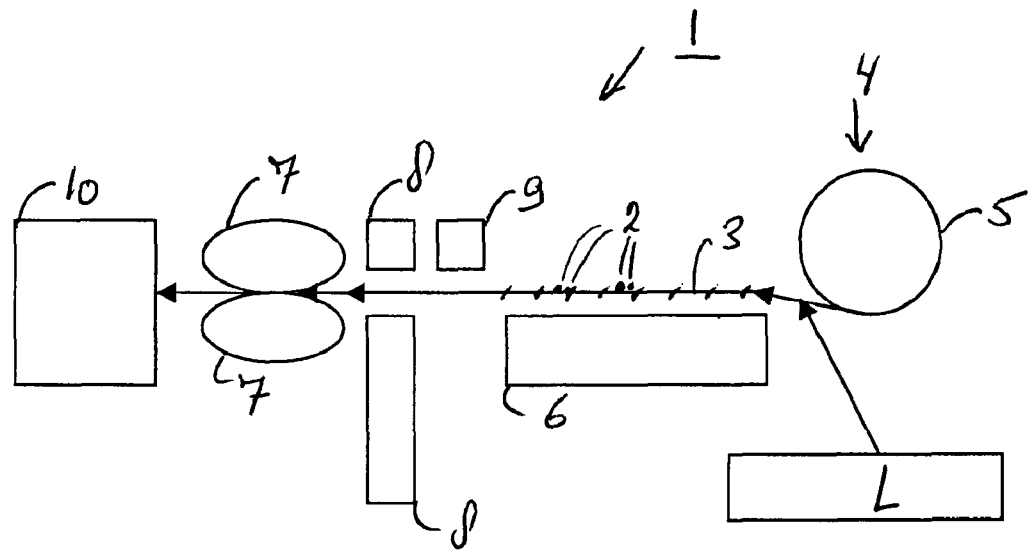

The present invention relates to an inspection device, comprising:
- means by which interconnected, substantially flat bags containing one or more objects are provided;
- vibrating means which set the objects in at least one of said bags vibrating;
- optical means for recording one or more images of said objects;
- conveying means for conveying set bags.

The present invention also relates to a method wherein interconnected, substantially flat bags are provided, in which bags objects are present which are set vibrating, after which one or more images of the objects in the bag are recorded; and also to a string of bags obtained by means of said method and/or said device.

Such a device or method is known from WO 2004/072626, in which a string of consecutive object-filled bags are subjected to a mechanical impulse, which moves the objects in the bags apart. Said impulse is imparted by one or more flaps provided with cams, which strike against the underside of a conveyor belt on which the bags are being conveyed. Subsequently, one or more images of the moved-apart objects are recorded for inspection and identification purposes.

A drawback of the known inspection device is the fact that it produces comparatively much noise and vibrations during operation.

The object of the present invention is to provide a quiet and reliable inspection device in which the above drawbacks have been obviated.

In order to accomplish that object, the inspection device according to the invention is characterised in that said vibrating means are configured as means that vibrate in the plane of the interconnected bags, and in that said conveying means are configured as means that exert a squeezing force on the objects and a pulling force on the bags.

Accordingly, the method according to the invention is characterised in that said vibration is imparted to the objects in the plane of the interconnected bags, whilst a squeezing force effected by means of a pulling force on the bags is exerted on the vibrating objects.

The advantage of the inspection device and method according to the invention is that said vibration is exerted on the objects in the plane of the bags, causing the objects in each of the bags to move apart. The bags are not subjected to impacts, therefore, they are not lifted and the objects do not jump up and down inside the bags during said vibration; all this in contrast to the aforesaid International (PCT) patent application WO 2004/072626. This results in a reduced noise level during operation of the inspection device according to the invention.

The invention further provides a higher degree of reliability upon moving apart and subsequently checking and inspecting the objects, since a virtually noiseless vibration in the plane of the bags is combined with conveying said bags under such a tension in said plane that the flat sides of the bags are subjected to a pulling force. As a result of said pulling force, a squeezing force is exerted on the objects during or after said vibration, which squeezing force causes the objects in the bags to move apart or keeps said objects apart, thus making it possible to record one or more images having a higher degree of reliability.

In addition, in contrast to the aforesaid PCT patent application a separate conveyor belt below and/or above the string of interconnected bags is not needed, so that it becomes possible to realise a simpler and lighter design of the device and method according to the invention.

Furthermore, less mechanical and electrical power is needed, because the vibration is only generated in the plane of the bags, without the bags and the objects moving up and down, whilst the—weaker—vibration reduces the risk of the objects breaking. In this way the identification by means of the device and method according to the invention will take place with an enhanced degree of reliability.

One embodiment of the device according to the invention is characterised in that the conveying means are further configured as means which exert a pulling force on the bags, which may or may not take place while the bags are being conveyed along the means moving in the plane of said bags.

By exerting a certain pulling force on the string of interconnected bags both while said bags are stationary and while said bags are moving, the objects that were moved apart by the vibration in question at an earlier stage will remain in place, making it possible to record a good identifying image.

Another embodiment of the device according to the invention is characterised in that the conveying means are configured as continuously or intermittently driven means.

In principle an intermittent transport, i.e. the bags are alternately stationary and in motion, of the string of bags being under mechanical tension is possible. The images are recorded while the bags are stationary in that case.

Advantageously, however, the interconnected bags are continuously kept in motion, because the level of vibrations and objectionable noise is even further reduced in that case. The camera in the optical means does not need to move along in that case, but it may be stationary relative to the inspection device, providing it is sufficiently fast, i.e. has a sufficiently short recording time.

To that end, however, the movement of the objects during the time in which a recording of the bag is made must be negligible, so that a good quality of the recording remains ensured. In a preferred embodiment of the method according to the invention, the minor movement (in that case) during the recording time will hardly affect the detection quality of the objects.

Further preferred embodiment variants of the inspection device and method according to the invention are defined in the other claims.

Figure 2:
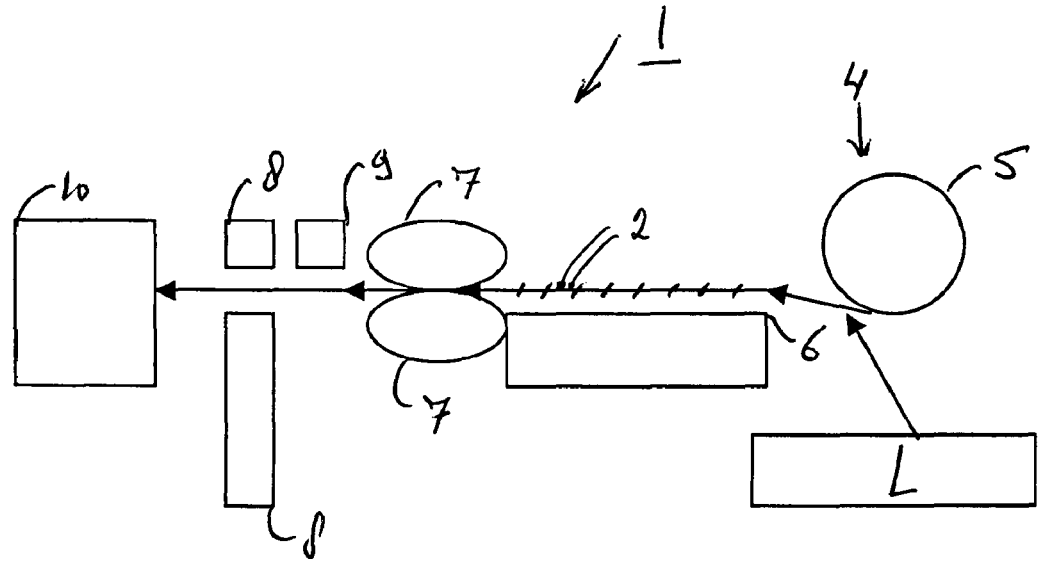

The inspection device and method according to the present invention will now be explained in more detail with reference to the figures below, in which corresponding parts are provided with the same numerals. In the drawing:

FIG. 1 shows a first possible embodiment of an inspection device according to the present invention; and FIG. 2 shows a second possible embodiment of an inspection device according to the present invention.

FIGS. 1 and 2 each show an embodiment of an inspection device 1 as used for inspecting, identifying and checking objects 2 (schematically indicated), usually tablets, capsules and the like, which are contained in bags 3 strung together to form a string of bags. The inspection device 1 comprises means 4 for providing the interconnected, substantially flat bags 3. The bag-providing means 4 are provided with a roller mechanism in this embodiment, which comprises a rotatable reel 5 in this embodiment, on which the string of bags 3 is wound. Via rollers (not shown in the figures), which may be spring-loaded, the string of bags 3 is directed away from the reel 5, preferably via a free-hanging loop (schematically indicated L). The advantage of this is that the loop forms a kind of reference for conveying the bags through the device 1 with substantially the same desired pulling force (yet to be explained hereinafter) on the bags at all times. This effect can also be achieved, however, by mounting brake means on the reel 5 or on the rotary shaft thereof.

After being unwound from the reel 5, possibly via the loop L, the string of bags arrives at the vibrating means 6 forming part of the device 1, which set the objects in the bags vibrating. Said vibration takes place in the plane of the interconnected, substantially flat bags, with the vibrating means possibly comprising a preferably horizontally extending vibrating plate 6, over which the bags can be simply transported, without additional clamping means for the bags or the objects, which are usually positioned above the bags, being required. The vibration, which takes place in a direction substantially parallel to the flat surface of the bags, stirs the objects just enough to move them apart within the bags and distribute them over a flat inner side of the bag, as it were, so that the risk of the objects touching or overlapping each other after being subjected to the aforesaid vibration is minimal.

The device 1 further comprises conveying means 7 for conveying the bags 3 through the device 1. The conveying means 7 are configured as means that exert a squeezing force on the objects 2, i.e. means that exert a pulling force on the bags. Also the brake means on the reel 5 and/or the loop L may be considered to be included in the pulling means 7, because in certain circumstances they can also contribute to setting up a sufficient pull in the bags 3. Both flat sides of a bag are subjected to a pulling force in longitudinal direction, which may or may not take place during the conveying movement, i.e. possibly also while the string of bags 3 is stationary, so that said sides tend to move towards each other, as a result of which the desired squeezing force, which also contributes towards preventing the objects from overlapping, is exerted on the objects.

The device 1 further comprises optical means 8 for recording one or more, usually digital, images of the objects.

FIG. 1 shows an embodiment of the inspection device 1 in which the optical means 8 are disposed directly behind the vibrating plate 6 (shown in a horizontal position), whilst FIG. 2 shows an embodiment in which the optical means 8 are disposed downstream of the conveying means. The conveying means 7 are generally provided with a roller mechanism, in this embodiment represented as rotatable conveyor rollers 7, between which the bags are clamped and by means of which the string of bags is moved through the device 1. The conveying means 7 comprise (generally electric) motors (not shown), which drive the string of bags continuously or intermittently, i.e. in start-stop mode. Preferably, a desired mechanical tension is maintained in the longitudinal direction of the strung-together bags 3 both during standstill and during transport. In the embodiment shown in FIG. 2, said tension may have been gradually decreased after the bags have passed the conveyor rollers 7, without this leading to the objects 2 shifting within the bags 3 and overlapping or coming into too close contact with each other, which would make it more difficult to realise a reliable inspection and identification.

The bags are clamped between the aforesaid conveyor rollers 7 and subjected to a pulling force in the longitudinal direction, to the left in FIGS. 1 and 2. A variant that might be used in the case of a more direct transport of the string of bags might for example comprise a pair of sprockets, which engage in transport openings to be provided on either side of the string of bags in that case. The mechanical tension could still be exerted in the longitudinal direction in that case, but it could (also) be exerted in transverse direction, with the same desired result of effecting a squeezing force on the objects 2 in the bags 3.

If the string of bags is conveyed intermittently through the device, at least one image of a bag will be recorded each time the bags are stationary. Standstill, however, takes place at the expense of the number of bags that can be inspected per unit time and leads to jolting movements, which may shift the objects. This in contrast to a continuous movement of the bags, during which the pulling force on the bags or the conveying velocity thereof might nevertheless be varied, if desired. In the case of a continuous movement, the optical means 8 must record an image in such a short time that the distance over which the objects in question are transported during said time is practically negligible and does not lead to the quality of the recording being affected to any significant extent. The current CCD cameras are so fast that the string of bags can continue to move at a (practically) constant velocity without the end result being adversely affected to any noticeable extent. It is furthermore advantageous in that regard if images are recorded while using, in part, backlight of possibly different frequencies.

The optical means 8 are connected to a processing and data storage unit (not shown). Said processing unit runs software which analyses the recorded images, which may or may not be in colour, and links them to patient files, from which the software reads whether the correct number of tablets and the correct kind or the correct tablets, capsules, pills or the like are indeed present in the inspected bag. Said reading or the scanning in a scanner 9 of an identification code or bar code previously printed on each bag, together with combining the bar code information with the information read from the bag and the patient information, is one of the measures to rule out the possibility of incorrect medication somehow being administered to a patient at some point. A printer unit may be connected to the device 1 for providing rejected or approved bags with an appropriate print, so that a sorting machine 10 disposed downstream of the inspection device 1 will separate the two types of bags and, if necessary, gather the numbers of bags intended for specific patients and produce a report on said activities.

The invention claimed is:

1. An inspection device, comprising:
   a bag providing mechanism which provides interconnected, substantially flat bags containing one or more objects;
   a vibration mechanism which sets the objects in at least one of said bags vibrating;
   an optical mechanism which records one or more images of said objects;
   a conveying mechanism which conveys set bags by exerting a pulling force on the bags,
   wherein said vibration mechanism is configured to vibrate in the plane of the interconnected bags, and
   wherein said conveying mechanism is configured to exert a squeezing force on the objects and the pulling force on the bags.

2. A device according to claim 1, wherein said conveying mechanism is further configured to exert a pulling force on the bags, which may or may not take place while the bags are being conveyed along the vibration mechanism moving in the plane of said bags.

3. A device according to claim 1, wherein said conveying mechanism is configured to be continuously or intermittently driven.

4. A device according to claim 1, wherein said vibration mechanism is disposed under the bags.

5. A device according to claim 1, wherein said vibration mechanism is a vibrating plate.

6. A device according to claim 1, wherein said vibration mechanism is arranged in a substantially horizontal position.

7. A device according to claim 1, wherein said conveying mechanism is disposed downstream and/or upstream of said optical mechanism.

8. A device according to claim 1, wherein said bag-providing mechanism and/or said conveying mechanism is provided with a roller mechanism which directly or indirectly engages the bags.

9. A device according to claim 8, wherein said roller mechanism is provided with a brake mechanism.

10. A plurality of strings of interconnected bags obtained by using the device according to claim 1.

11. A method of providing bags for inspection, comprising:
providing interconnected, substantially flat bags, in which bags objects are present which are set vibrating, after which one or more images of the objects in the bag are recorded,
wherein said vibration is imparted to the objects in the plane of the interconnected bags, whilst a squeezing force effected by means of a pulling force on the bags is exerted on the vibrating objects.

12. A method according to claim 11, wherein said vibration is exerted on the objects while the bags are being transported or while the bags are stationary.

13. A method according to claim 11, wherein said pulling force is exerted continuously or intermittently.

14. A method according to claim 11, wherein a distance over which the objects are moved during the time a recording of the objects is made is practically negligible in relation to the quality of the recording.

15. A method according to claim 11, wherein the bags are passed over a vibration mechanism.

16. A method according to claim 15, wherein said vibration mechanism sets a vibration substantially in the horizontal plane.

17. A method according to claim 11, wherein said at least one image is recorded before or after the interconnected bags pass the conveying mechanism.

18. A method according to claim 11, wherein after the interconnected bags have been provided, said bags are arranged in a free- hanging loop before being set vibrating.

19. A method according to claim 11, wherein said pulling force is generated through direct or indirect engagement of the bags and/or the objects.

20. A plurality of strings of interconnected bags obtained by the method according to claim 11.

* * * * *